US011896206B2

(12) United States Patent
Sapir

(10) Patent No.: US 11,896,206 B2
(45) Date of Patent: *Feb. 13, 2024

(54) TREATMENT OF APPENDAGE OPENINGS

(71) Applicant: TRANSSEPTAL SOLUTIONS LTD., Kefar Monash (IL)

(72) Inventor: Elad Sapir, Kefar Vitkin (IL)

(73) Assignee: TRANSSEPTAL SOLUTIONS LTD., Kefar Monash (IL)

(*) Notice: Subject to any disclaimer, the term of this patent is extended or adjusted under 35 U.S.C. 154(b) by 654 days.

This patent is subject to a terminal disclaimer.

(21) Appl. No.: 16/262,280

(22) Filed: Jan. 30, 2019

(65) Prior Publication Data

US 2019/0159766 A1 May 30, 2019

Related U.S. Application Data

(63) Continuation of application No. 15/619,626, filed on Jun. 12, 2017, now Pat. No. 10,238,371, which is a
(Continued)

(51) Int. Cl.
*A61B 5/02* (2006.01)
*A61B 17/00* (2006.01)
(Continued)

(52) U.S. Cl.
CPC ........ *A61B 17/0057* (2013.01); *A61B 5/0044* (2013.01); *A61B 5/02028* (2013.01); *A61B 5/1076* (2013.01); *A61B 5/1079* (2013.01); *A61B 5/6856* (2013.01); *A61B 17/3478* (2013.01); *A61B 17/12122* (2013.01);
(Continued)

(58) Field of Classification Search
CPC .............. A61B 17/0057; A61B 5/0044; A61B 5/02028; A61B 5/1076; A61B 5/1079; A61B 5/6856; A61B 17/3478
See application file for complete search history.

(56) References Cited

U.S. PATENT DOCUMENTS 4,677,990 A 7/1987 Neubauer
5,010,892 A 4/1991 Colvin et al.
(Continued)

FOREIGN PATENT DOCUMENTS

DE 102005023414 11/2006
EP 0808607 11/1997
(Continued)

OTHER PUBLICATIONS

An International Search Report and a Written Opinion both dated Sep. 30, 2014, which issued during the prosecution of Applicant's PCT/IL2014/050338.
(Continued)

*Primary Examiner* — Daniel L Cerioni
(74) *Attorney, Agent, or Firm* — Sughrue Mion, PLLC

(57) ABSTRACT

A method is provided for measuring an opening of an appendage of an atrium of a subject, the method including inserting a catheter into the atrium of the subject using a transvenous approach. Thereafter, at least one loop is deployed from a wall of the catheter, such that a distal end of the loop is distal to a distal end of the catheter. Thereafter, the loop is used to measure the opening of the appendage. Other embodiments are also described.

8 Claims, 15 Drawing Sheets

Related U.S. Application Data continuation of application No. 15/258,210, filed on Sep. 7, 2016, now Pat. No. 9,706,982, which is a continuation-in-part of application No. 14/636,759, filed on Mar. 3, 2015, now Pat. No. 9,668,674.

(51) Int. Cl.
| | | |
|---|---|---|
| *A61B 5/107* | (2006.01) | |
| *A61B 5/00* | (2006.01) | |
| *A61B 17/34* | (2006.01) | |
| *A61B 90/00* | (2016.01) | |
| *A61B 17/12* | (2006.01) | |

(52) U.S. Cl.
CPC ............. *A61B 2017/00243* (2013.01); *A61B 2017/00247* (2013.01); *A61B 2017/00632* (2013.01); *A61B 2090/061* (2016.02); *A61B 2090/3966* (2016.02); *A61B 2576/023* (2013.01)

(56) References Cited

U.S. PATENT DOCUMENTS

| | | |
|---|---|---|
| 5,042,161 A | 8/1991 | Hodge |
| 5,069,674 A | 12/1991 | Fearnot et al. |
| 5,329,923 A | 7/1994 | Lundquist |
| 5,489,296 A | 2/1996 | Love et al. |
| 5,497,774 A | 3/1996 | Swartz |
| 5,507,743 A | 4/1996 | Edwards |
| 5,571,215 A * | 11/1996 | Sterman ........... A61B 17/00234 128/898 |
| 5,573,520 A | 11/1996 | Schwartz et al. |
| 5,605,543 A | 2/1997 | Swanson |
| 5,639,276 A | 6/1997 | Weinstock et al. |
| 5,741,429 A | 4/1998 | Donadio et al. |
| 5,807,395 A | 9/1998 | Mulier et al. |
| 5,865,791 A * | 2/1999 | Whayne ........... A61B 17/00234 604/500 |
| 5,885,228 A | 3/1999 | Rosenman et al. |
| 5,910,150 A | 6/1999 | Saadat |
| 6,033,359 A | 3/2000 | Doi |
| 6,102,926 A | 8/2000 | Tartaglia |
| 6,575,921 B2 | 6/2003 | Vanden Hoek et al. |
| 6,623,448 B2 | 9/2003 | Slater |
| 6,623,449 B2 | 9/2003 | Paskar |
| 6,629,534 B1 | 10/2003 | St. Goar et al. |
| 6,641,564 B1 | 11/2003 | Kraus |
| 6,650,923 B1 | 11/2003 | Lesh |
| 6,761,708 B1 | 7/2004 | Chiu et al. |
| 6,796,963 B2 | 9/2004 | Carpenter et al. |
| 6,863,677 B2 | 3/2005 | Breznock |
| 7,048,733 B2 | 5/2006 | Hartley |
| 7,279,003 B2 | 10/2007 | Berra et al. |
| 7,344,543 B2 | 3/2008 | Sra |
| 7,581,328 B2 | 9/2009 | Greenhalgh et al. |
| 7,615,014 B2 | 11/2009 | Omata et al. |
| 7,635,353 B2 | 12/2009 | Gurusamy |
| 7,641,638 B2 | 1/2010 | Waxman et al. |
| 7,654,970 B2 | 2/2010 | Dubey et al. |
| 7,666,203 B2 | 2/2010 | Chanduszko |
| 7,708,704 B2 | 5/2010 | Mitelberg et al. |
| 7,815,577 B2 | 10/2010 | Krishnan |
| 7,824,341 B2 | 11/2010 | Krishnan |
| 7,850,644 B2 | 12/2010 | Gonzalez |
| 7,976,551 B1 | 7/2011 | Gutfinger |
| 8,000,809 B2 | 8/2011 | Elencwajg |
| 8,012,106 B2 | 9/2011 | Mangiardi et al. |
| 8,019,404 B2 | 9/2011 | Kapadia |
| 8,029,470 B2 | 10/2011 | Whiting et al. |
| 8,114,110 B2 | 2/2012 | Bednarek |
| 8,172,757 B2 | 5/2012 | Jaffe |
| 8,235,986 B2 | 8/2012 | Kulesa |
| 8,251,963 B2 | 8/2012 | Chin et al. |
| 8,292,910 B2 | 10/2012 | Chanduszko et al. |
| 8,317,810 B2 | 11/2012 | Stangenes |
| 8,353,898 B2 | 1/2013 | Lutze et al. |
| 8,491,619 B2 | 7/2013 | Breznock |
| 8,663,168 B2 | 3/2014 | Chin et al. |
| 8,694,077 B2 | 4/2014 | Kapadia |
| 8,747,459 B2 | 6/2014 | Nguyen et al. |
| 8,771,297 B2 | 7/2014 | Millet et al. |
| 8,911,384 B2 | 12/2014 | Santiago |
| 8,961,550 B2 | 2/2015 | Lenker et al. |
| 9,005,139 B2 | 4/2015 | Klaiman et al. |
| 9,339,230 B2 | 5/2016 | Kassab |
| 9,345,574 B2 | 5/2016 | Conklin |
| 9,545,265 B2 | 1/2017 | Maisano et al. |
| 9,668,674 B2 | 6/2017 | Sapir |
| 9,700,351 B2 | 7/2017 | Maisano et al. |
| 9,706,982 B2 | 7/2017 | Sapir |
| 9,788,858 B2 | 10/2017 | Maisano et al. |
| 10,238,371 B2 | 3/2019 | Sapir |
| 2002/0026175 A1 | 2/2002 | Paskar |
| 2002/0038129 A1 | 3/2002 | Peters et al. |
| 2002/0058960 A1 | 5/2002 | Hudson et al. |
| 2002/0143291 A1 | 10/2002 | Slater |
| 2002/0169377 A1 | 11/2002 | Khairkhahan |
| 2003/0125709 A1 | 7/2003 | Eidenschink |
| 2003/0144657 A1 | 7/2003 | Bowe |
| 2003/0191523 A1 | 10/2003 | Hojeibane |
| 2004/0220471 A1 | 11/2004 | Schwartz |
| 2004/0225212 A1 * | 11/2004 | Okerlund ............... A61B 6/503 600/407 |
| 2004/0225304 A1 | 11/2004 | Vidlund et al. |
| 2005/0101984 A1 | 5/2005 | Chanduszko et al. |
| 2005/0149097 A1 | 7/2005 | Regnell |
| 2005/0149115 A1 * | 7/2005 | Roue ................. A61B 17/0401 606/213 |
| 2005/0177132 A1 | 8/2005 | Lentz et al. |
| 2005/0197623 A1 | 9/2005 | Leeflang et al. |
| 2005/0216018 A1 | 9/2005 | Sennett |
| 2006/0064062 A1 | 3/2006 | Gurusamy et al. |
| 2006/0074398 A1 | 4/2006 | Whiting et al. |
| 2006/0142756 A1 | 6/2006 | Davies et al. |
| 2006/0241564 A1 | 10/2006 | Corcoran et al. |
| 2006/0241583 A1 | 10/2006 | Malecki et al. |
| 2006/0276710 A1 | 12/2006 | Krishnan |
| 2007/0270741 A1 | 11/2007 | Hassett |
| 2008/0021405 A1 | 1/2008 | Jacobsen et al. |
| 2008/0097398 A1 | 4/2008 | Mitelberg et al. |
| 2008/0140173 A1 | 6/2008 | Eskaros et al. |
| 2008/0161840 A1 | 7/2008 | Osiroff |
| 2008/0188928 A1 | 8/2008 | Salahieh et al. |
| 2008/0243183 A1 | 10/2008 | Miller et al. |
| 2009/0171276 A1 | 7/2009 | Bednarek et al. |
| 2009/0312755 A1 | 12/2009 | Thapliyal et al. |
| 2010/0022948 A1 | 1/2010 | Wilson |
| 2010/0042110 A1 * | 2/2010 | Kelley ............... A61B 17/3468 606/129 |
| 2010/0168777 A1 | 7/2010 | Stangenes |
| 2010/0228276 A1 | 9/2010 | Breznock |
| 2011/0054487 A1 | 3/2011 | Farnan |
| 2011/0082538 A1 | 4/2011 | Dahlgren et al. |
| 2011/0251594 A1 | 10/2011 | Godin |
| 2011/0270239 A1 | 11/2011 | Werneth |
| 2011/0295107 A1 | 12/2011 | Kargar et al. |
| 2011/0313283 A1 | 12/2011 | Kapadia |
| 2012/0010503 A1 | 1/2012 | Mangiardi |
| 2012/0022427 A1 | 1/2012 | Kapadia |
| 2012/0065597 A1 | 3/2012 | Cohen |
| 2012/0179188 A1 | 7/2012 | Chanduszko |
| 2012/0277730 A1 | 11/2012 | Salahieh et al. |
| 2013/0123620 A1 | 5/2013 | Tekulve |
| 2013/0274784 A1 | 10/2013 | Lenker |
| 2014/0081302 A1 | 3/2014 | Thapliyal et al. |
| 2014/0081305 A1 | 3/2014 | Breznock et al. |
| 2014/0309675 A1 | 10/2014 | Maisano et al. |
| 2014/0309678 A1 | 10/2014 | Maisano et al. |
| 2014/0309679 A1 | 10/2014 | Maisano et al. |
| 2014/0343538 A1 | 11/2014 | Lenker et al. |
| 2015/0173592 A1 * | 6/2015 | Leeflang ............... A61B 1/313 600/106 |

(56) References Cited

U.S. PATENT DOCUMENTS

| | | | |
|---|---|---|---|
| 2016/0015513 A1* | 1/2016 | Lashinski | A61F 2/2445 623/2.37 |
| 2016/0100859 A1 | 4/2016 | Sapir et al. | |
| 2016/0100860 A1 | 4/2016 | Lenker et al. | |
| 2016/0256075 A1 | 9/2016 | Sapir | |
| 2016/0374656 A1 | 12/2016 | Sapir | |
| 2017/0105761 A1 | 4/2017 | Sapir et al. | |
| 2017/0281005 A1 | 10/2017 | Sapir | |

FOREIGN PATENT DOCUMENTS

| | | |
|---|---|---|
| WO | 2011/130456 | 10/2011 |
| WO | 2013/128461 | 9/2013 |
| WO | 2014/064694 | 5/2014 |
| WO | 2014/170890 | 10/2014 |
| WO | 2016/059638 | 4/2016 |

OTHER PUBLICATIONS

U.S. Appl. No. 61/811,947, filed Apr. 15, 2013.
An Office Action dated Sep. 9, 2015, which issued during the prosecution of U.S. Appl. No. 14/245,135.
An Office Action dated Feb. 9, 2016, which issued during the prosecution of U.S. Appl. No. 14/245,135.
An Office Action dated Jan. 21, 2016, which issued during the prosecution of U.S. Appl. No. 14/287,523.
An Office Action dated Jan. 22, 2016, which issued during the prosecution of U.S. Appl. No. 14/287,470.
U.S. Appl. No. 62/095,150, filed Dec. 22, 2014.
An International Preliminary Report on Patentability dated Oct. 20, 2015, which issued during the prosecution of Applicant's PCT/IL2014/050338.
An Invitation to pay additional fees dated Jan. 15, 2016, which issued during the prosecution of Applicant's PCT/IL2015/051026.
An International Search Report and a Written Opinion both dated Mar. 30, 2016, which issued during the prosecution of Applicant's PCT/IL2015/051026.
An Office Action dated Aug. 23, 2016, which issued during the prosecution of U.S. Appl. No. 14/513,435.
An Office Action dated Jul. 21, 2016, which issued during the prosecution of U.S. Appl. No. 14/287,523.
Notice of Allowance dated Sep. 15, 2016, which issued during the prosecution of U.S. Appl. No. 14/287,470.
An Office Action dated Sep. 28, 2016, which issued during the prosecution of U.S. Appl. No. 14/636,759.
An Office Action dated Oct. 21, 2016, which issued during the prosecution of U.S. Appl. No. 14/245,135.
An Office Action dated Apr. 12, 2017, which issued during the prosecution of U.S. Appl. No. 14/287,523.
An Office Action dated Feb. 23, 2017, which issued during the prosecution of U.S. Appl. No. 14/513,435.
An Office Action dated Mar. 3, 2017, which issued during the prosecution of U.S. Appl. No. 15/258,210.
Notice of Allowance dated May 19, 2017, which issued during the prosecution of U.S. Appl. No. 14/245,135.
Notice of Allowance dated May 26, 2017, which issued during the prosecution of U.S. Appl. No. 15/258,210.
An Advisory Action dated Feb. 7, 2017, which issued during the prosecution of U.S. Appl. No. 14/245,135.
HHS Tube—Fort Wayne Metals—downloaded from http://www.fwmetals.com/products/hhs-tube/ Jan. 8, 2017—this product was commercially available sufficiently earlier than the effective U.S. filing date and any foreign priority date of the present application.
An Office Action dated Sep. 11, 2018, which issued during the prosecution of U.S. Appl. No. 15/619,626.
An Office Action dated Mar. 14, 2018, which issued during the prosecution of U.S. Appl. No. 15/619,626.
Notice of Allowance dated Nov. 7, 2018, which issued during the prosecution of U.S. Appl. No. 15/619,626.
A Non-Final Office Action in U.S. Appl. No. 15/649,110, dated Nov. 30, 2020.
A Final Office Action issued in U.S. Appl. No. 15/649,110, dated Jun. 17, 2021.

* cited by examiner

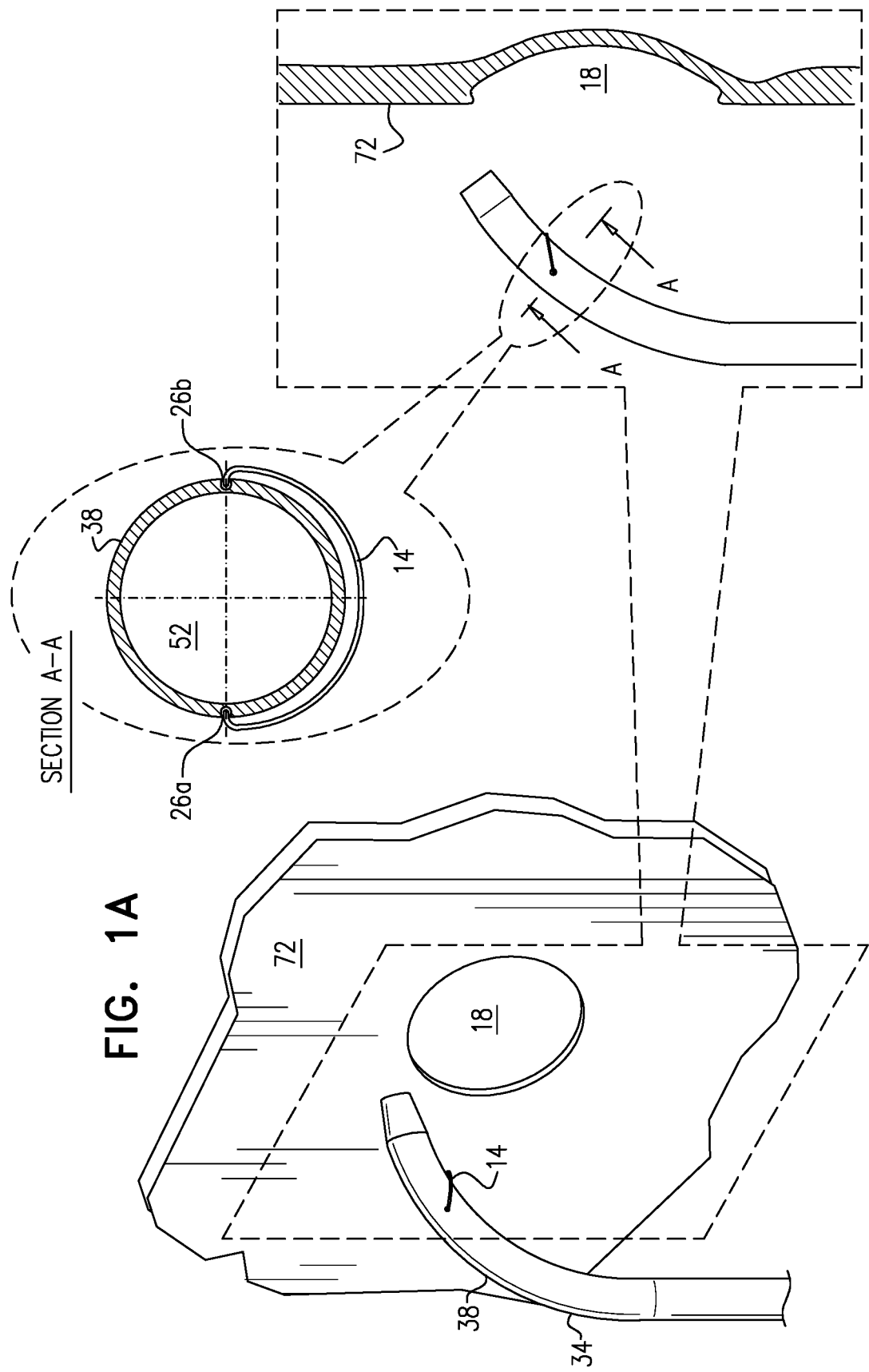

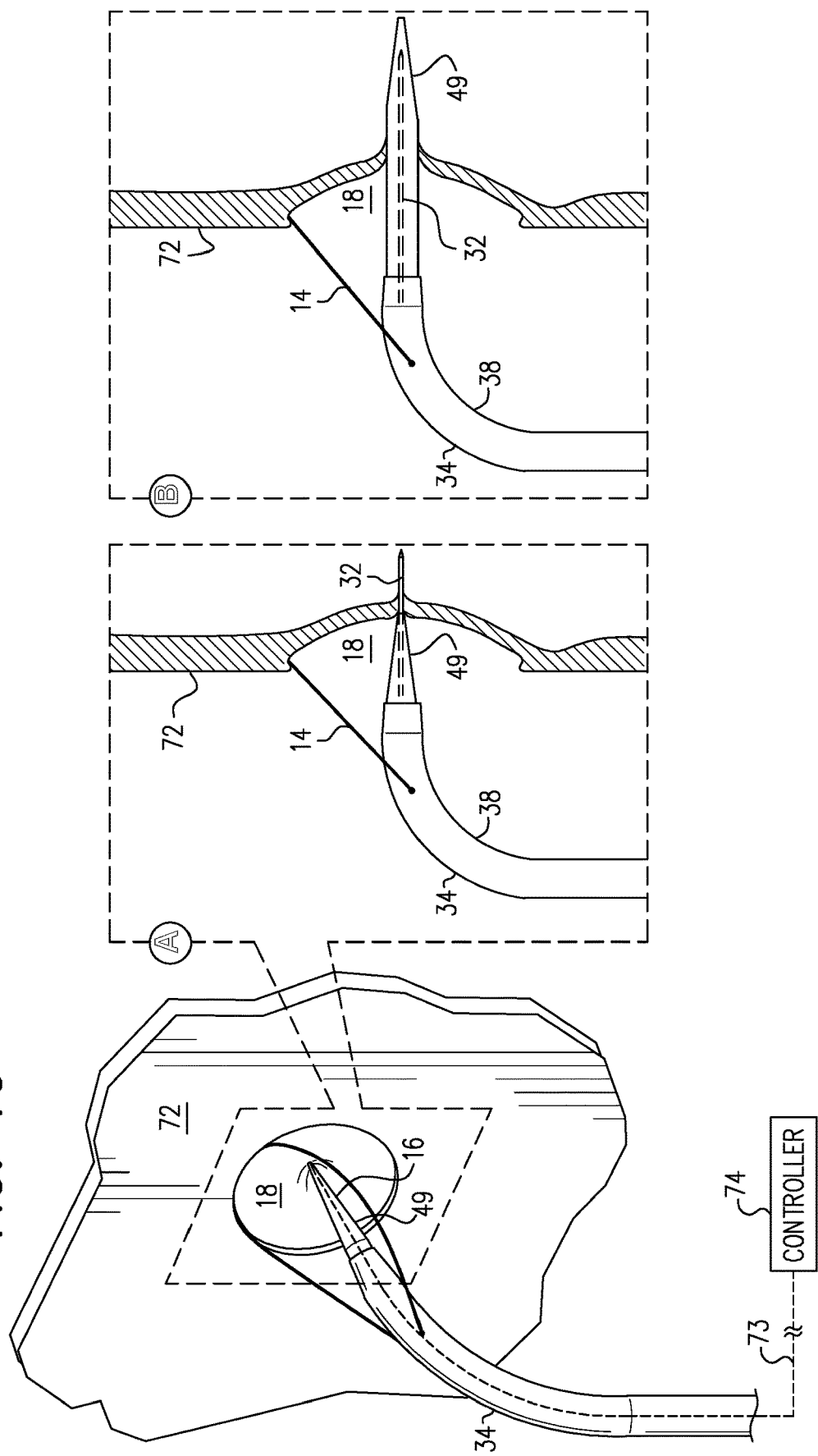

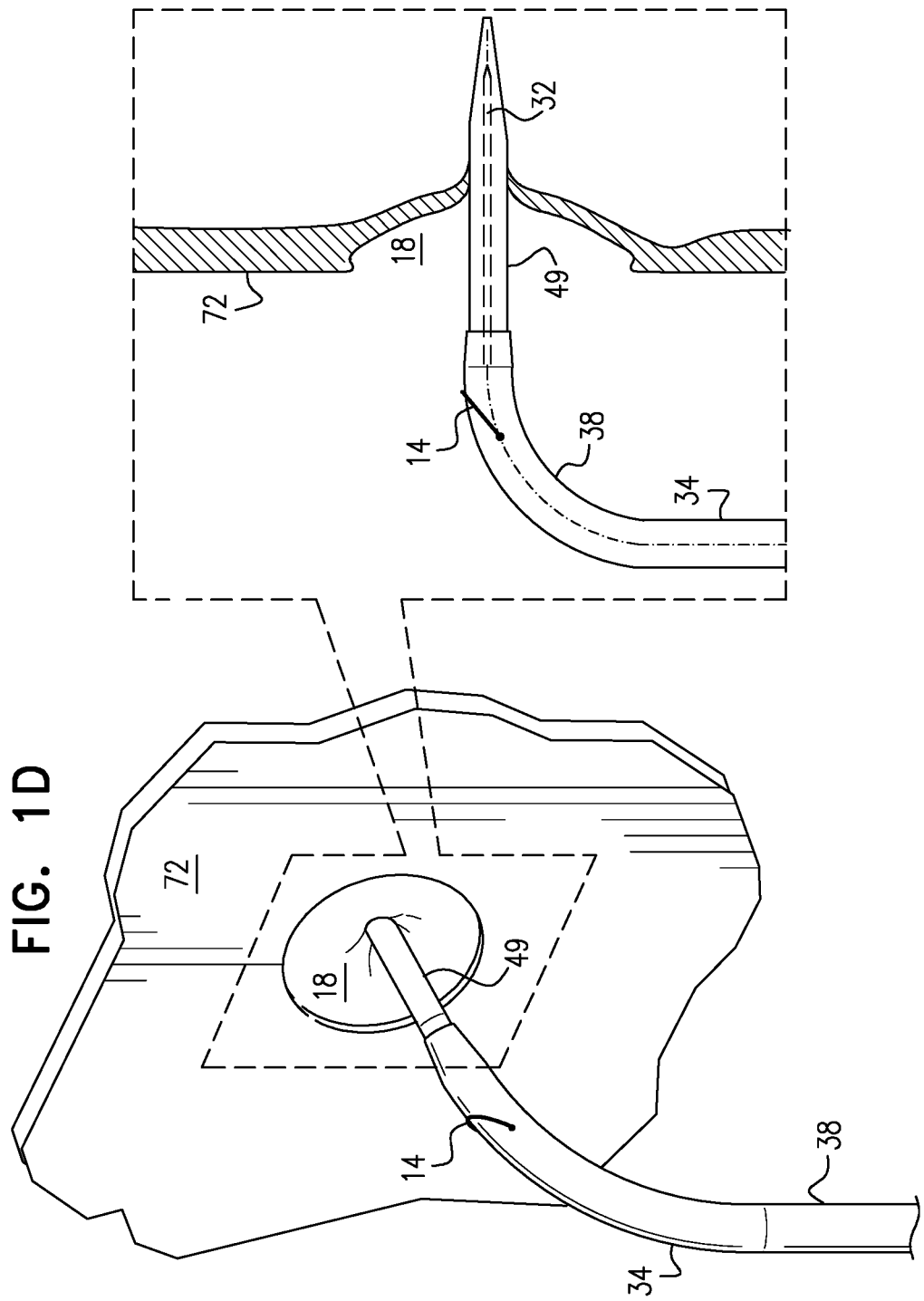

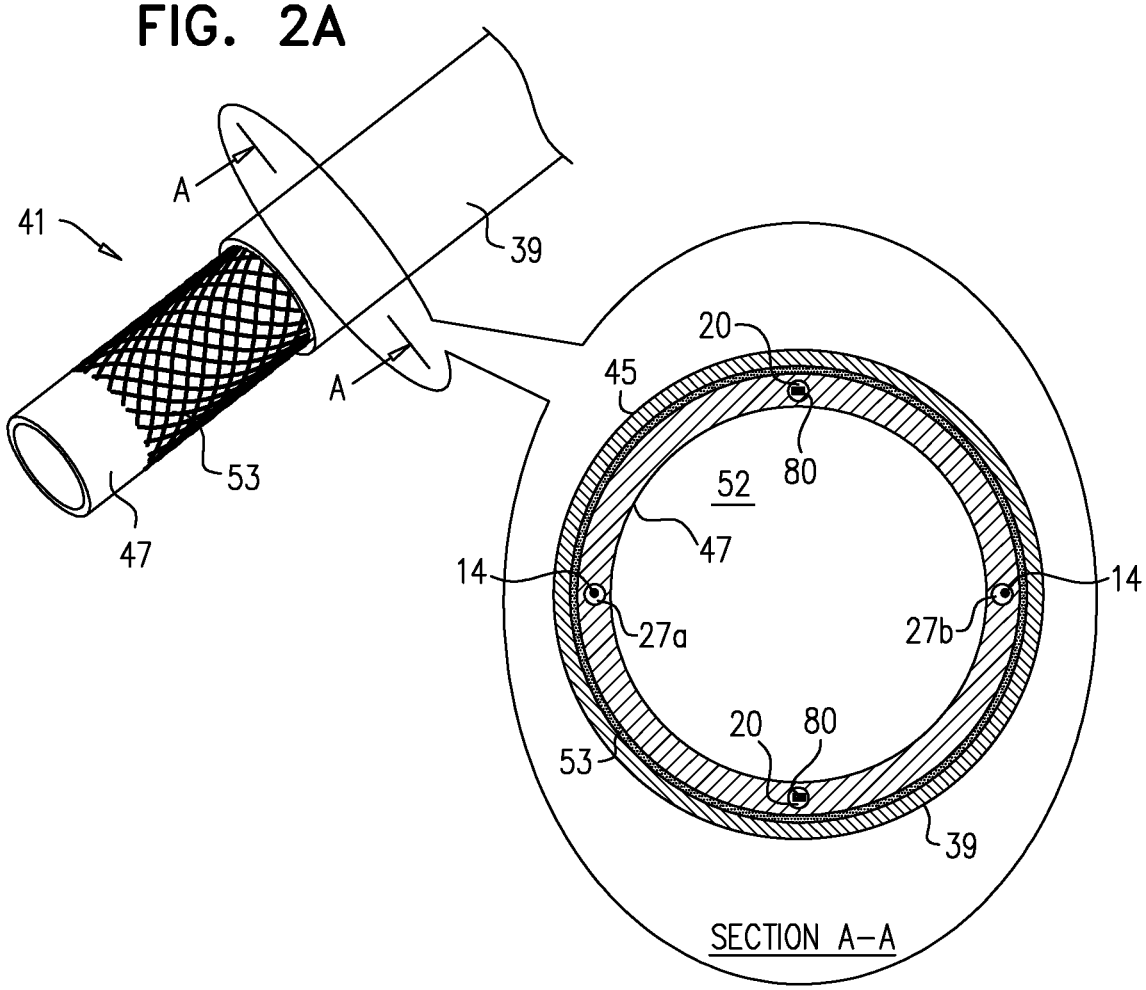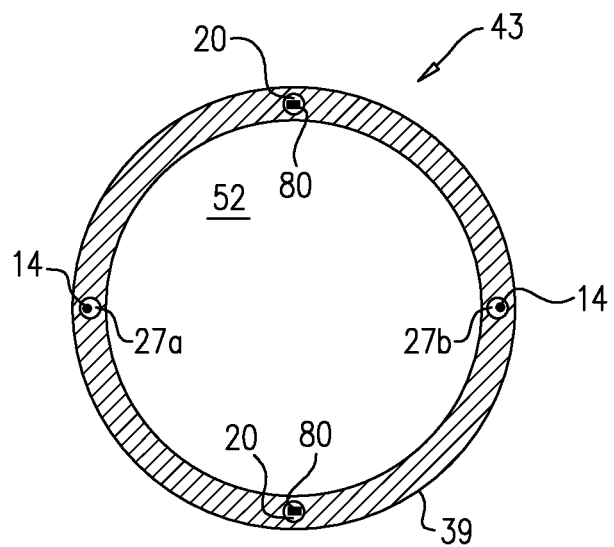

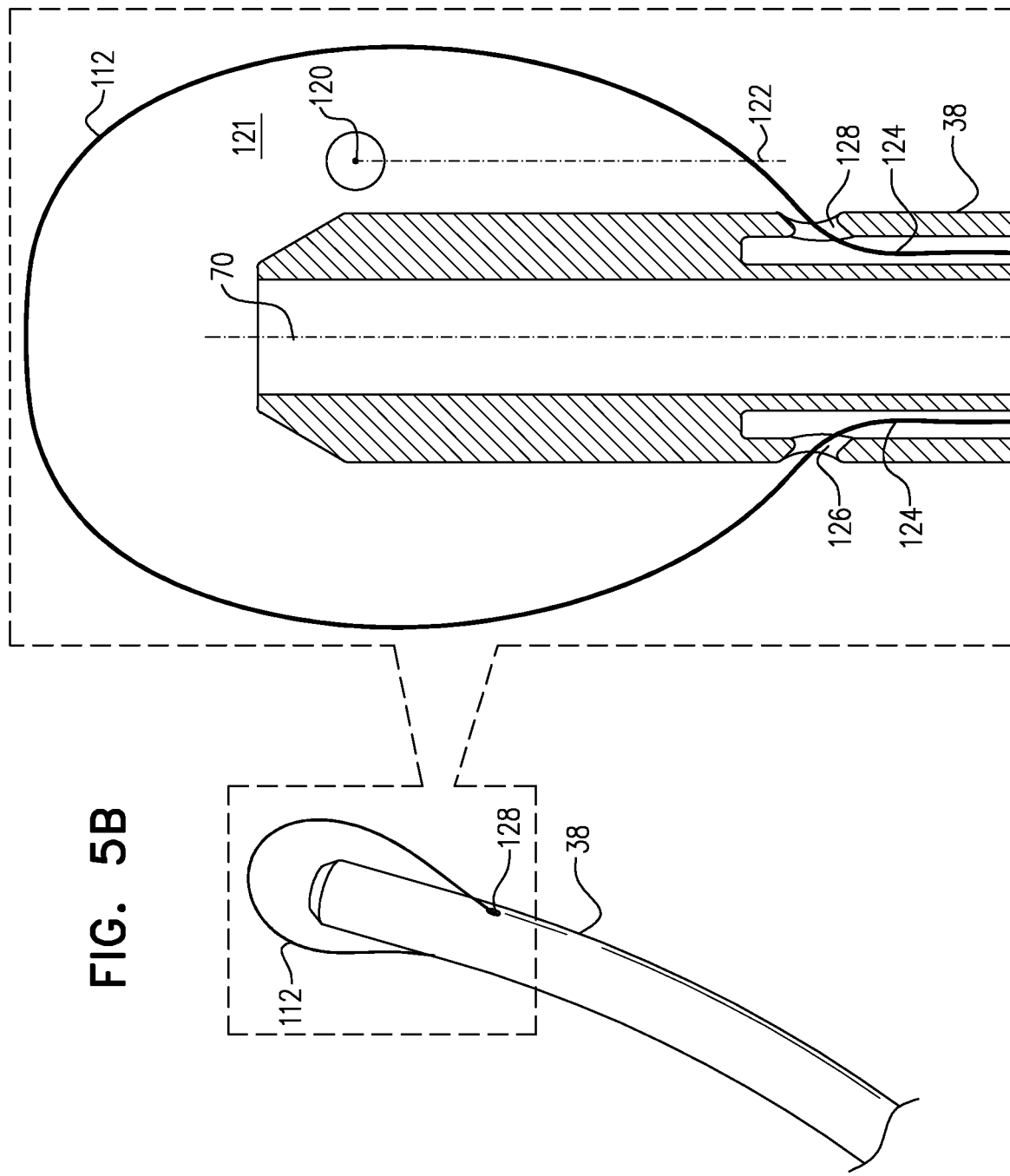

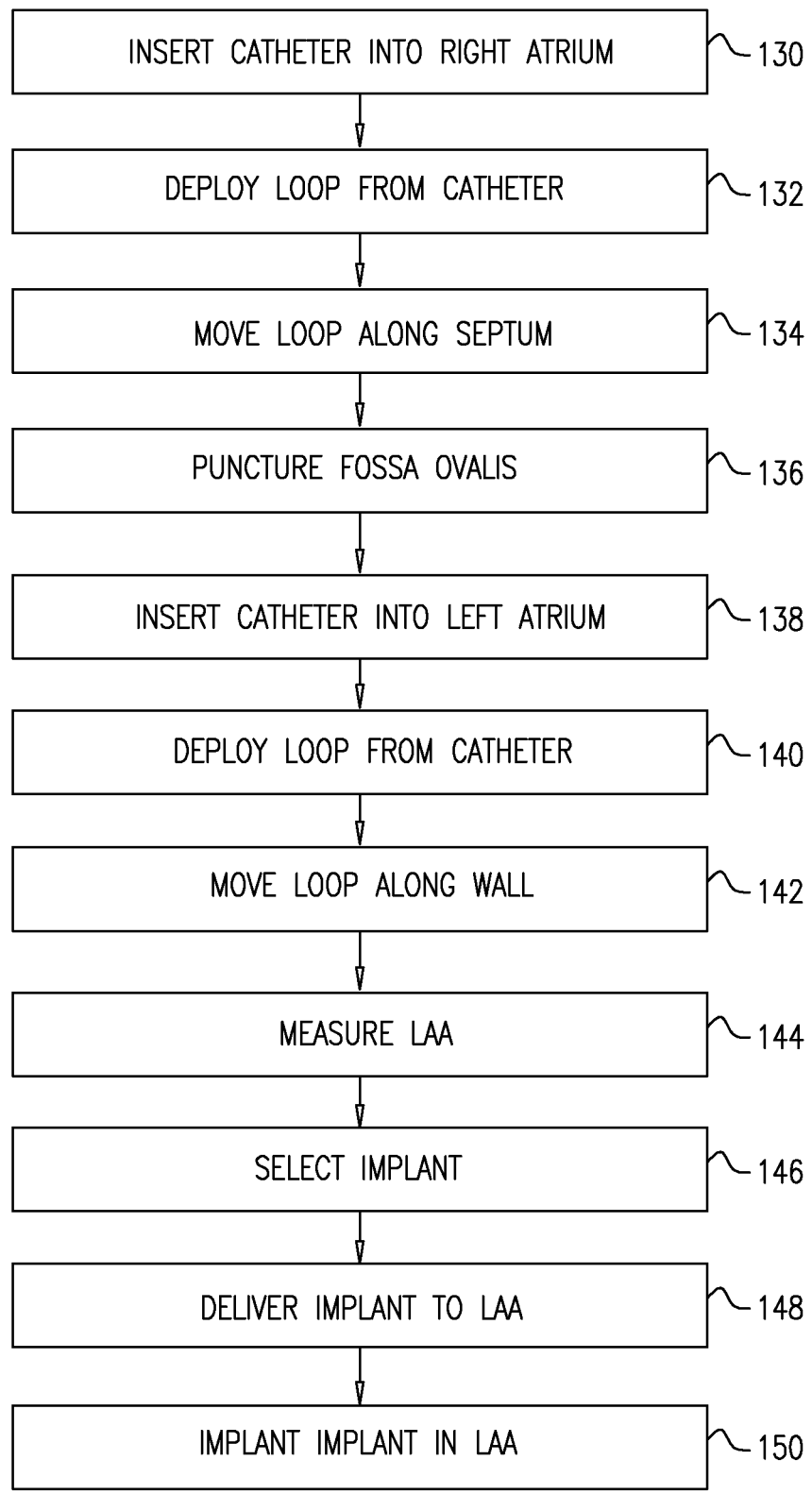

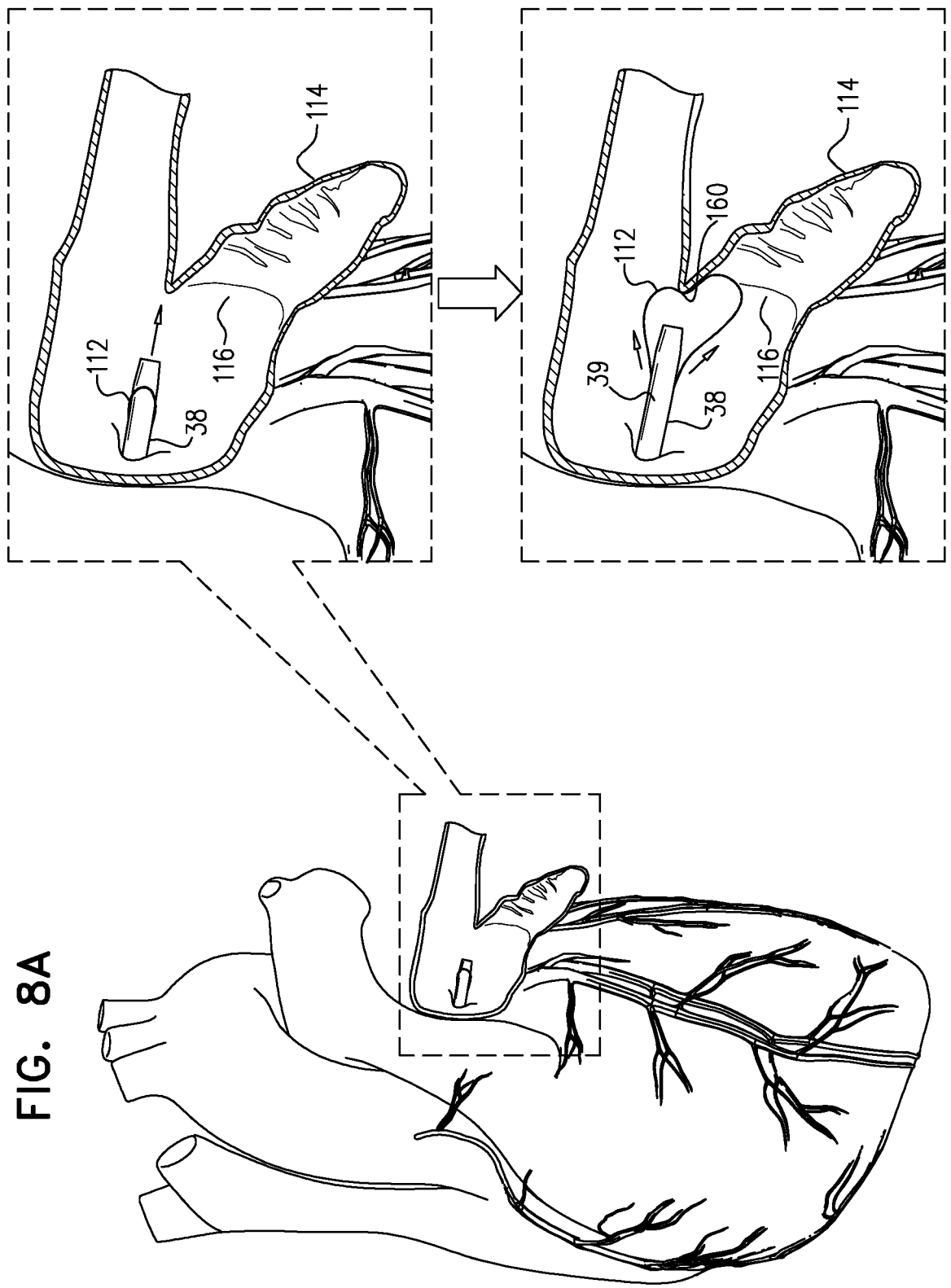

TREATMENT OF APPENDAGE OPENINGS

CROSS-REFERENCE TO RELATED APPLICATIONS

The present application is a continuation of U.S. application Ser. No. 15/619,626, filed Jun. 12, 2017, now U.S. Pat. No. 10,238,371, which is a continuation of U.S. application Ser. No. 15/258,210, filed Sep. 7, 2016, now U.S. Pat. No. 9,706,982, which is a continuation-in-part of U.S. application Ser. No. 14/636,759, filed Mar. 3, 2015, now U.S. Pat. No. 9,668,674, which is assigned to the assignee of the present application and is incorporated herein by reference.

FIELD OF THE INVENTION

Applications of the present invention relate to finding and/or measuring openings inside a human body, such as an opening of a left atrial appendage (LAA).

BACKGROUND

In some cases, a subject may require an implant to close off his left atrial appendage.

SUMMARY OF THE INVENTION

Applications of the present invention include a method for measuring an opening of an appendage of an atrium (e.g., a left atrial appendage (LAA)) of a subject, e.g., for purposes of implanting an implant at the opening. A catheter is inserted into the atrium, and at least one loop is deployed from a wall of the catheter, such that the distal end of the loop is distal to the distal end of the catheter. The loop is used to measure the opening of the appendage.

For some applications, the loop is partially inserted into an appendage of the atrium, and, while the loop is being inserted, a portion of a perimeter of an opening of the appendage is atraumatically contacted with a portion of the loop. Thereafter, the loop is further inserted into the appendage, and, using the loop, a size of the opening of the appendage is measured.

There is therefore provided, in accordance with an application of the present invention, a method including:
  inserting a catheter into an atrium of a subject;
  deploying at least one loop from a wall of the catheter, such that a distal end of the loop is distal to a distal end of the catheter;
  inserting the loop partially into an appendage of the atrium, and, while inserting the loop, atraumatically contacting a portion of a perimeter of an opening of the appendage with a portion of the loop;
  thereafter, further inserting the loop into the appendage; and
  thereafter, using the loop, measuring a size of the opening of the appendage.

For some applications, the method does not include inserting a guidewire into the appendage.

For some applications, atraumatically contacting the portion of the perimeter of the opening of the appendage with the portion of the loop includes locally bending the portion of the loop against the portion of the perimeter of the opening.

For some applications, the method further includes, before measuring the size of the opening, identifying a location of the opening by imaging the atrium and the appendage.

For some applications, the method further includes, before measuring the size of the opening:
  moving the distal end of the loop along a wall of the atrium; and
  identifying the opening in response to the distal end of the loop reaching the opening.

For some applications, the method further includes:
  in response to the measured size of the opening, selecting an implant of an appropriate size;
  delivering the implant from the catheter to the appendage; and
  implanting the implant at least partially in the appendage.

For some applications, delivering the implant to the appendage includes using the loop to guide the distal end of the catheter into the appendage.

For some applications, delivering the implant to the appendage includes advancing the distal end of the catheter into the appendage without advancing the distal end of the catheter over a guidewire inserted into the appendage.

For some applications, the catheter is an outer catheter, and delivering the implant from the catheter includes advancing an inner delivery catheter through the outer catheter while the implant is disposed within the inner delivery catheter.

For some applications, deploying the loop from the wall of the catheter includes deploying the loop from a lateral wall of the catheter.

For some applications, the opening is an opening of an appendage of a left atrium of the subject, and inserting the catheter includes inserting the catheter into the left atrium.

For some applications:
  the method further includes, prior to inserting the catheter into the left atrium:
    inserting the catheter into a right atrium of the subject; and
    puncturing a hole through a fossa ovalis by passing a puncturing element out of the distal end of the catheter, and
  inserting the catheter into the left atrium includes passing the catheter through the hole into the left atrium.

For some applications:
  the loop is an appendage-perimeter-contacting loop,
  the method further includes, prior to puncturing the hole through the fossa ovalis and after inserting the catheter into the right atrium:
    deploying at least one fossa-ovalis-finding loop from the wall of the catheter; and
    moving the fossa-ovalis-finding loop along an interatrial septum of the subject, until the fossa-ovalis-finding loop contacts a fossa ovalis of the subject, and
  puncturing the fossa ovalis includes puncturing the fossa ovalis, in response to the fossa-ovalis-finding loop contacting the fossa ovalis, by passing the puncturing element out of the distal end of the catheter.

For some applications, the fossa-ovalis-finding loop is the appendage-perimeter-contacting loop.

For some applications, the fossa-ovalis-finding loop is different from the appendage-opening-contacting loop.

For some applications, puncturing the hole includes mechanically puncturing the fossa ovalis using the puncturing element.

For some applications, puncturing the hole includes applying, using the puncturing element, energy to the fossa ovalis that is capable of creating the hole through the fossa ovalis.

For some applications, measuring the size of the opening includes:

expanding the loop until the loop contacts at least two points on the perimeter of the opening; and measuring a distance between the points, by using imaging to view the loop while it is in contact with the points.

For some applications, measuring the size of the opening includes:

expanding the loop until the loop contacts at least two points on the perimeter of the opening; and measuring a distance between the points, by utilizing a marker on a proximal portion of the loop that indicates an extent to which the loop has been expanded.

For some applications:

the loop includes a longitudinal member that passes through a first opening and a second opening in the catheter wall, and deploying the loop includes deploying the loop by passing the longitudinal member through at least one of the first and second openings.

For some applications, deploying the at least one loop includes deploying at least two loops.

For some applications, deploying the at least two loops includes deploying more than two loops.

For some applications, deploying the loop includes deploying the loop such that a normal to a plane defined by the loop intersects a line that is parallel to a longitudinal axis of the catheter at an angle that is between 10 and 90 degrees.

For some applications, measuring the size of the opening of the appendage includes measuring (a) a distance between a first pair of points on the perimeter of the opening, and (b) a distance between a second pair of points on the perimeter of the opening.

There is further provided, in accordance with some applications or the present invention, a method for measuring an opening of an appendage of an atrium of a subject, the method including:

inserting a catheter into the atrium of the subject;

deploying at least one loop from wall of the catheter, such that a distal end of the loop is distal to a distal end of the catheter; and using the loop to measure the opening of the appendage.

In some applications, deploying the loop from the wall of the catheter includes deploying the loop from a lateral wall of the catheter.

In some applications, the method includes measuring an opening of an appendage of a left atrium of the subject.

In some applications, deploying the loop includes deploying the loop such that a normal to a plane defined by the loop intersects a line that is parallel to a longitudinal axis of the catheter at an angle that is between 10 and 90 degrees.

In some applications, the method further includes, before measuring the opening:

moving the distal end of the loop along a wall of the atrium; and identifying the opening in response to the distal end of the loop reaching the opening.

In some applications, the method further includes:

in response to the measuring, selecting an implant of an appropriate size;

delivering the implant to the opening, by passing the implant through the catheter; and implanting the implant in the opening.

In some applications, measuring the opening includes:

expanding the loop until the loop contacts at least two points on a perimeter of the opening; and measuring a distance between the points, by using imaging to view the loop while it is in contact with the points.

In some applications, measuring the opening includes:

expanding the loop until the loop contacts at least two points on a perimeter of the opening; and measuring a distance between the points, by utilizing a marker on a proximal portion of the loop that indicates an extent to which the loop has been expanded.

In some applications:

the atrium is a left atrium, the loop is an appendage-finding loop, and the method further includes, prior to inserting the catheter into the left atrium:

inserting the catheter into a right atrium of the subject;

deploying at least one fossa-ovalis-finding loop from the wall of the catheter;

moving the fossa-ovalis-finding loop along an interatrial septum of the subject, until the fossa-ovalis-finding loop contacts a fossa ovalis of the subject; and in response to the fossa-ovalis-finding loop contacting the fossa ovalis, puncturing the fossa ovalis by passing a puncturing element out of the distal end of the catheter.

In some applications, the fossa-ovalis-finding loop is the appendage-finding loop.

In some applications, the fossa-ovalis-finding loop is different from the appendage-finding loop.

In some applications:

the loop includes a longitudinal member that passes through a first opening and a second opening in the catheter wall, and deploying the loop includes deploying the loop by passing the longitudinal member through at least one of the first and second openings.

In some applications, deploying the at least one loop includes deploying at least two loops.

In some applications, deploying the at least two loops includes deploying more than two loops.

In some applications, measuring the opening of the appendage includes measuring (a) a distance between a first pair of points on a perimeter of the opening, and (b) a distance between a second pair of points on the perimeter of the opening.

The present invention will be more fully understood from the following detailed description of applications thereof, taken together with the drawings, in which:

BRIEF DESCRIPTION OF THE DRAWINGS

FIGS. 1A-D are schematic illustrations of apparatus for puncturing a fossa ovalis of a subject, in accordance with some applications of the present invention;

FIGS. 2A-B are schematic illustrations of a cross-section of a wall of a catheter, in accordance with some applications of the present invention;

FIGS. 5A-B are schematic illustrations of apparatus used for finding and/or measuring an opening of an appendage of an atrium, in accordance with respective applications of the present invention;

FIG. 7 is a flowchart for a method for implanting an implant in a left atrial appendage (LAA) of a subject, in accordance with some applications of the present invention;

FIGS. 8A-D are schematic illustrations of a method for finding and/or measuring an opening of an LAA of a subject, in accordance with some applications of the present invention.

DETAILED DESCRIPTION OF APPLICATIONS

Figure 1B:
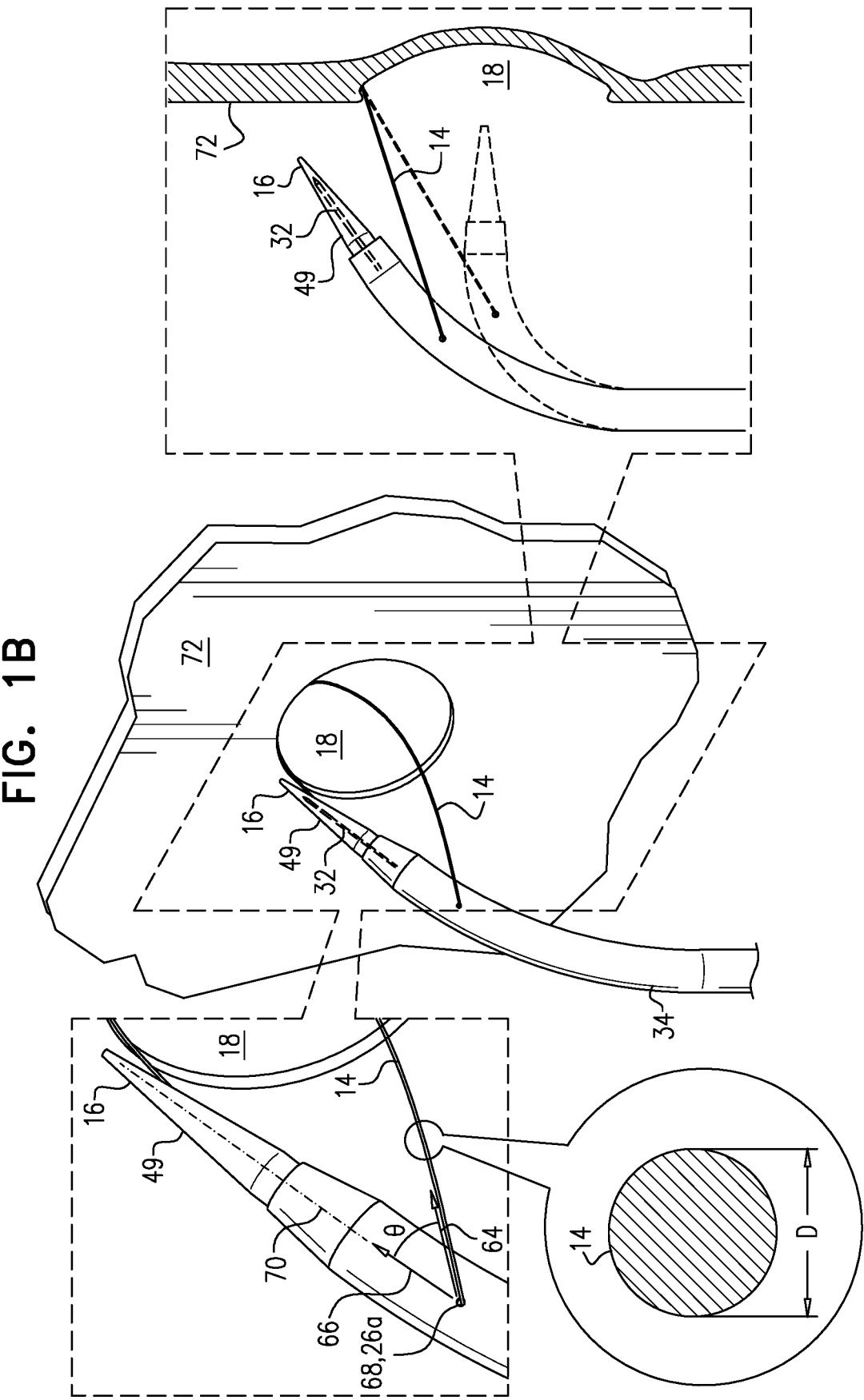

Reference is made to FIGS. 1A-D, which are schematic illustrations of apparatus 34 for puncturing a fossa ovalis 18 of a subject, in accordance with some applications of the present invention. Apparatus 34 comprises a catheter 38, which may also be referred to by those in the field as an introducer tube. Catheter 38 is shaped to define a catheter lumen 52.

Reference is also made to FIGS. 2A-B, which are schematic illustrations of a cross-section of a wall 39 of catheter 38, in accordance with some applications of the present invention. Wall 39 comprises a braided portion 41 (FIG. 2A), which has an outer surface 45, an inner surface 47, and a braided interior 53 between outer surface 45 and inner surface 47. Wall 39 also comprises an unbraided portion 43 (shown in cross-section in FIG. 2B), which is typically disposed proximally to braided portion 41. Wall is shaped to define a first longitudinally-running channel 27a and a second longitudinally-running channel 27b therethrough. (Channels 27a and 27b run through both the braided and unbraided portions.) A distal portion of catheter 38 is shaped to define a first lateral opening 26a and a second lateral opening 26b (FIG. 1A). A flexible longitudinal member 14 (e.g., a wire) passes (a) from a proximal portion of the catheter to the distal portion of the catheter via first channel 27a, (b) out of the first channel via first lateral opening 26a, (b) into second channel 27b via second lateral opening 26b, and (c) from the distal portion of the catheter to the proximal portion of the catheter via the second channel.

Typically, flexible longitudinal member 14 is mechanically resilient, i.e., it does not readily buckle upon being subjected to a compressive force, as would, for example, a string. The flexible longitudinal member typically comprises nitinol, stainless steel, and/or chromium cobalt, and typically has a diameter D that is at least 0.1 mm and/or less than 0.5 mm.

Catheter 38 is typically inserted into a vein in the pelvic area of the subject (e.g., the femoral vein), advanced toward the heart through the inferior vena cava, and inserted into the right atrium of the subject's heart. (Typically, catheter 38 is contained within the lumen of a sheath during parts of the insertion and/or withdrawal of the catheter, such as to reduce the risk of damage to surrounding tissue.) Following the insertion into the right atrium, the distal portion of catheter 38 is advanced toward interatrial septum 72 of the heart (FIG. 1A). Subsequently, as shown in FIG. 1B, the following two steps are performed sequentially (in either order), or simultaneously:

(a) A needle 32 is inserted into catheter lumen 52. Needle 32 is shaped to be slidably disposed within the catheter lumen. Typically, a dilator element 49 shaped to define a dilator lumen is shaped to be slidably disposed within the catheter lumen, and the needle is shaped to be slidably disposed within the dilator lumen. The needle is inserted into the dilator lumen, and is advanced up to tip 16 of the dilator element. (Although dilator element 49 may also be embodied as a catheter, the present description refers exclusively to catheter 38—the "introducer tube"—as a catheter.)

(b) Flexible longitudinal member 14 is deployed from the catheter, such that (i) a deployed portion of the flexible longitudinal member is loop-shaped, and (ii) the needle is on a first side of the deployed portion of the flexible longitudinal member. Typically, the flexible longitudinal member is deployed such that a deployment angle theta of the flexible longitudinal member is at least 10 degrees and/or less than 80 degrees, e.g., between 30 and 60 degrees. Deployment angle theta is defined as the angle between (a) a vector 64 that is tangent to the flexible longitudinal member at an exit point 68 of the flexible longitudinal member, and is directed away from the catheter, and (b) a distally-directed vector 66 that is parallel to the longitudinal axis 70 of the catheter at exit point 68. (Exit point 68 is identical to one of openings 26a and 26b.) As described hereinabove, the flexible longitudinal member is deployed by passing the flexible longitudinal member through openings 26a and 26b.

The catheter is steered until fossa ovalis 18 (e.g., an inner perimeter of the fossa ovalis) is contacted with the deployed portion of the flexible longitudinal member, as shown in FIG. 1B. Following the contacting, needle 32 is deployed, typically while within dilator element 49, as shown in the figure. Further typically, as shown in FIG. 1C, dilator tip 16 is brought into contact with the fossa ovalis. The needle is then advanced through a distal opening of the dilator tip and through the fossa ovalis, thus puncturing a hole in the fossa ovalis. Dilator tip 16 then dilates an opening created by the needle.

As shown in FIG. 1B, prior to puncturing the fossa ovalis, the distal end of needle 32 is typically passed through the deployed portion of the flexible longitudinal member to a second side of the deployed portion of the flexible longitudinal member that is opposite the first side. (The distal end of the needle is typically passed through the loop while disposed inside of the dilator element.) Subsequently, while the distal end of the needle is on the second side of the deployed portion of the flexible longitudinal member, the deployed portion of the flexible longitudinal member is withdrawn toward the catheter (FIG. 1D).

Typically, catheter 38 is flexibly and/or rotatably steerable via control wires 80 running through control-wire channels 20. The steerability of catheter 38 facilitates better localization of the desired puncturing point.

Reference is again made to FIG. 1C. For some applications, needle 32 is electrically conductive, and is coupled by one or more conductors 73 to a controller 74, which comprises or is in electrical communication with an energy source. The controller is configured to drive needle 32 to apply an ablating current, e.g., an RF current, to puncture the fossa ovalis or interatrial septum 72. Alternatively, instead of using an ablating current, other energy may be applied, such as heat, ultrasound, or light (e.g., laser) energy. The energy-based puncturing may be performed instead of or in combination with the force-based mechanical puncturing by the needle described herein. For some applications, the distal tip of the needle is blunt.

Figure 3:
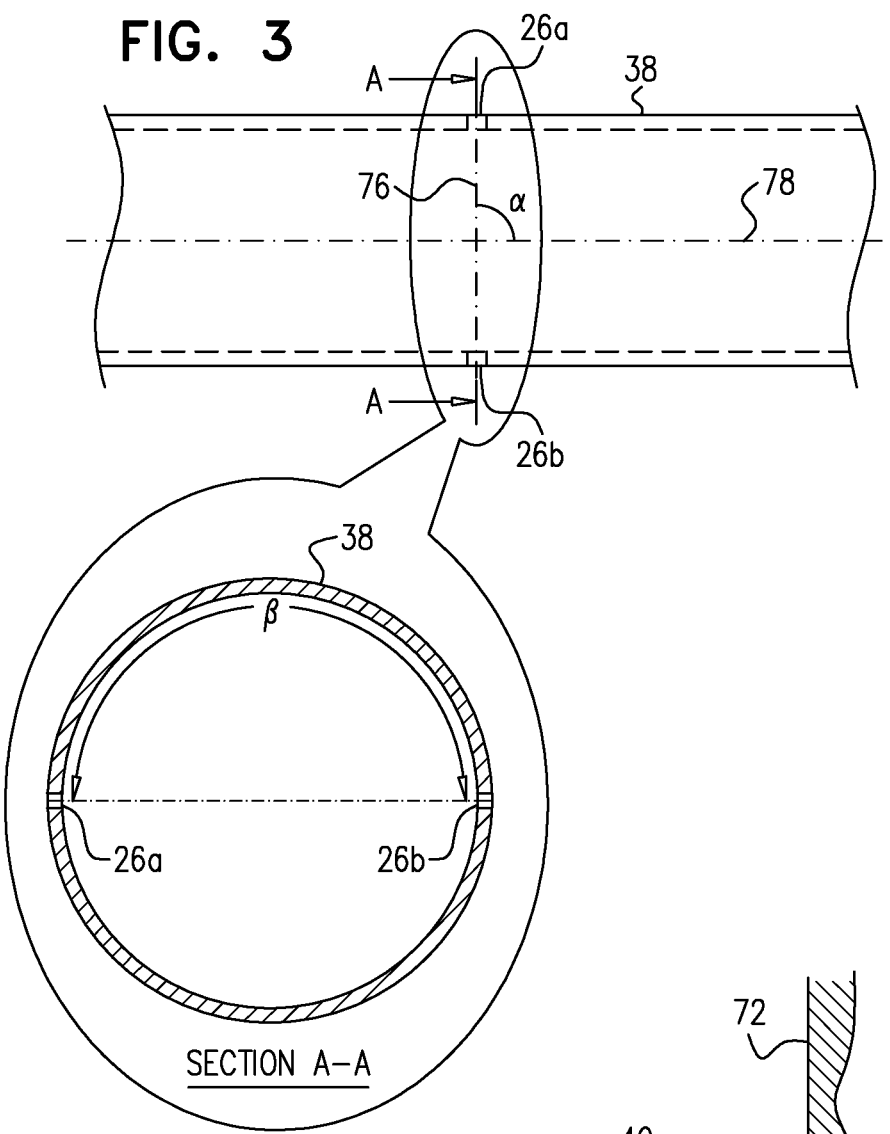
FIG. 3 is a schematic illustration of a catheter, in accordance with some applications of the present invention.

Reference is now made to FIG. 3, which is a schematic illustration of catheter 38, in accordance with some applications of the present invention. Typically, first and second openings 26a and 26b are disposed at substantially the same distance from the distal end of the catheter. An advantage of this disposition is that the loop may be deployed in a forward-facing direction, rather than laterally. For example, an angle alpha between (a) a first line 76 running between the first and second lateral openings, and (b) a second line 78 that is parallel to a central longitudinal axis of the catheter when the catheter is straight, may be at least 30 and/or less than 150 degrees, e.g., between 60 and 120 degrees, e.g., between 80 and 100 degrees. (An angle alpha of 90 degrees implies that the first and second openings are disposed at the same distance from the distal end of the catheter.) Alternatively or additionally, the distance of one opening from the distal end of the catheter differs by less than 1 cm from the distance of the other opening.

Further typically, the first and second openings are separated from one another by an angle beta of at least 170 degrees and/or less than 190 degrees (e.g., 180 degrees) measured along a circumference of the catheter. Thus, when the flexible longitudinal member is in its withdrawn position, it "occupies" only 170-190 degrees around the outside surface of the catheter, both prior to deployment and following withdrawal. In contrast, if beta were farther away from 180 degrees, the withdrawn flexible longitudinal member might occupy a relatively large angle, either prior to deployment or following withdrawal. For example, if beta were 90 degrees, the flexible longitudinal member would typically occupy 270 degrees either prior to deployment or following withdrawal, if, as described hereinabove with reference to FIG. 1D, the deployment and withdrawal of the flexible longitudinal member are done from/toward opposite sides of the catheter. It is typically preferred that such a large portion of the flexible longitudinal member not be disposed outside of the catheter when the flexible longitudinal member is in its withdrawn position, since the risk of collateral damage to tissue typically increases as more of the flexible longitudinal member is exposed. The angle beta of 170-190 degrees is thus advantageous, particularly when the deployment and withdrawal are done from/to opposite sides of the catheter. (It is noted that for some procedures or for some patients, an angle beta outside of 170-190 degrees is appropriate.)

Figure 4:
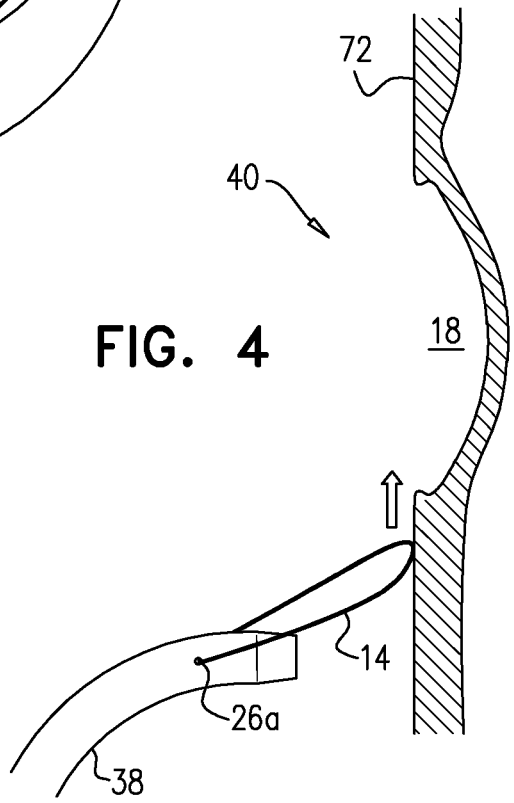
FIG. 4 is a schematic illustration of a method for puncturing the fossa ovalis, in accordance with some applications of the present invention.

Reference is now made to FIG. 4, which is a schematic illustration of a method 40 for puncturing the fossa ovalis, in accordance with sonic applications of the present invention. Before contacting the fossa ovalis with the deployed portion of flexible longitudinal member 14, the deployed portion of the flexible longitudinal member is moved along a surface of interatrial septum 72, until the flexible longitudinal member contacts the fossa ovalis. In some applications, as shown in FIG. 4, the deployed portion of the flexible longitudinal member is moved toward the fossa ovalis from below the fossa ovalis. In some applications, the flexible longitudinal member is radiopaque and/or is coupled to a plurality of radiopaque markers. In such applications, fluoroscopic imaging is used to view the flexible longitudinal member during and after deployment thereof. For example, fluoroscopic imaging may be used to view the flexible longitudinal member as it is moved toward the fossa ovalis, in order to help identify when the flexible longitudinal member has reached the fossa ovalis.

Figure 5A:
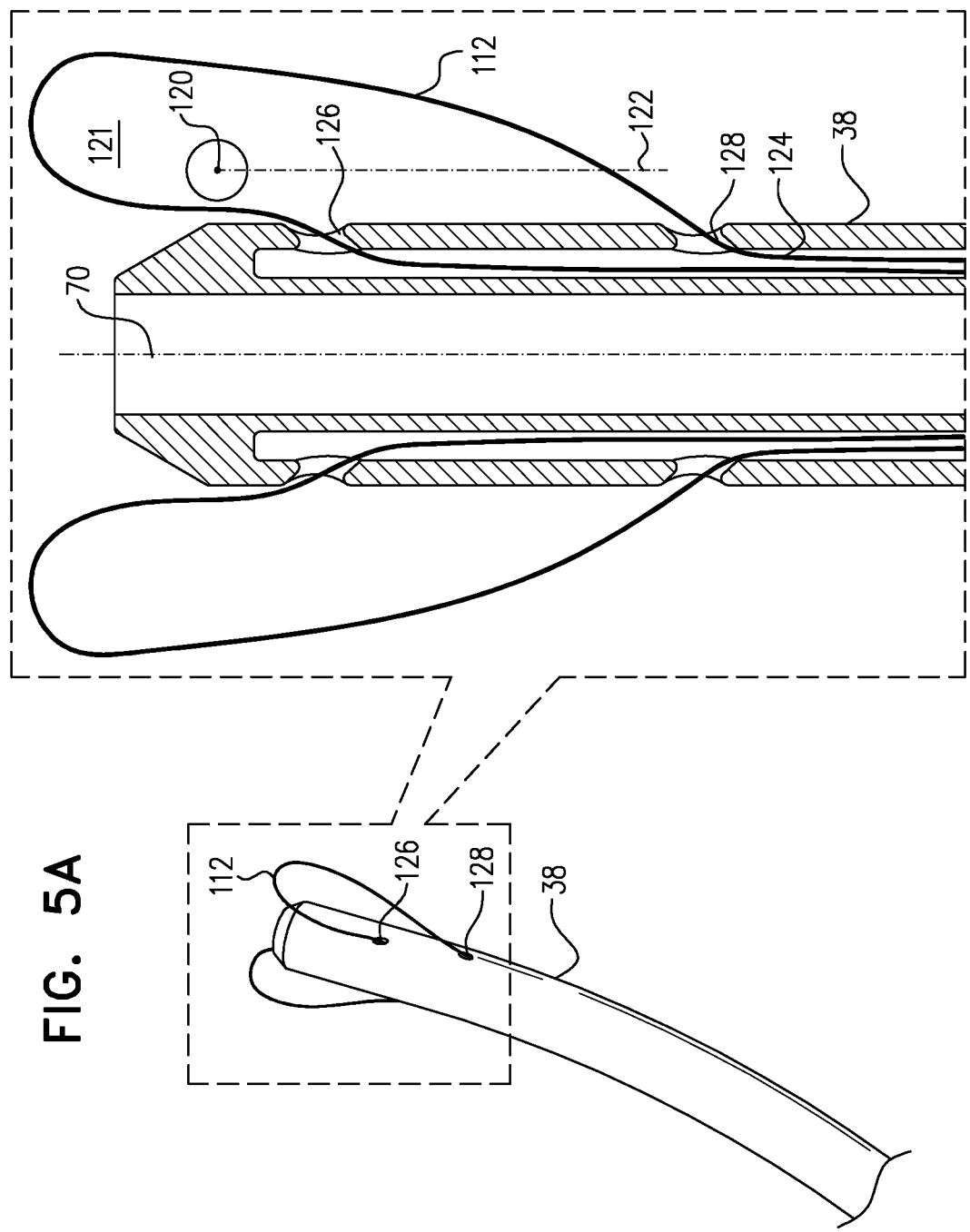

Reference is now made to FIGS. 5A-B, which are schematic illustrations of apparatus used for finding and/or measuring an opening of an appendage of an atrium (e.g., a left atrium) of a subject, in accordance with respective applications of the present invention. FIGS. 5A-B show cross-sections of catheter 38. One or more loops 112 are deployable from a wall (e.g., a lateral wall) of catheter 38 (FIG. 5A shows exactly one loop 112 and FIG. 5B shows exactly two loops 112). As described hereinbelow, loops 112 are appendage-finding and/or appendage-measuring loops, in that they may be used to find and/or measure the appendage of the atrium. In some applications, when finding and/or measuring the opening of the appendage, exactly one loop is deployed. In other applications, two or more loops are deployed.

To facilitate the finding and/or measuring of the opening, each loop 112 is deployed such that the distal end thereof is distal to the distal end of the catheter. Furthermore, each loop is deployed such that a normal 120 to a plane 121 defined by the loop intersects a line 122 that is parallel to longitudinal axis 70 of the catheter at an angle that is at least 10 and/or less than 90 degrees. For example, the cross-sections of FIGS. 5A-B show the loop (s) "in plane," such that normal 120 runs into the page, and the angle between the normal and line 122 is 90 degrees. In some applications, as shown in FIGS. 5A-B, each loop includes a longitudinal member 124 that passes through a first opening 126 and a second opening 128 in the catheter wall. In such applications, the loop is deployed by passing longitudinal member 124 through at least one of the first and second openings.

Figure 6A:
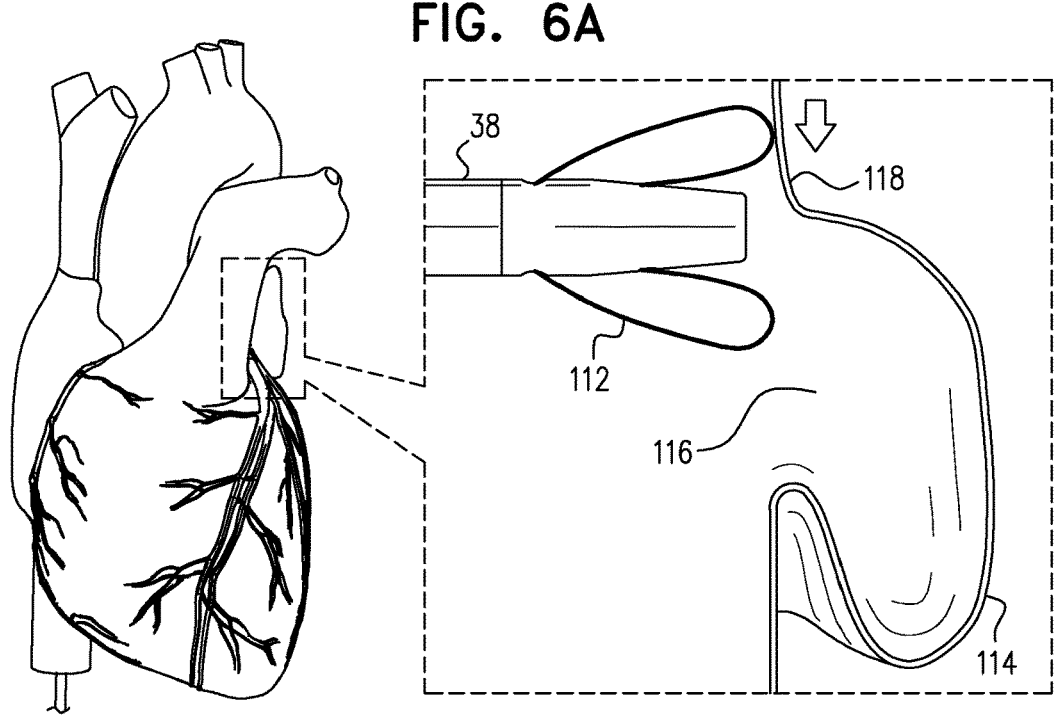
FIGS. 6A-E are schematic illustrations of a method for finding and/or measuring an opening of an appendage of an atrium, in accordance with some applications of the present invention.

Reference is now made to FIGS. 6A-E, which are schematic illustrations of a method for finding and/or measuring an opening 116 of an appendage (e.g., a left atrial appendage (LAA)) 114, in accordance with some applications of the present invention. FIG. 6A shows loops 112 being used to find opening 116. A distal end of at least one of the loops is moved along the wall 118 of the atrium, typically while being imaged. (For example, the loop may be radiopaque, and fluoroscopic imaging may be used to view the loop.) Upon reaching the opening, the loop loses contact with wall 118, and/or moves (e.g., "lunges" forward) into appendage 114. The loss of contact with the wall, and/or the moving into the appendage, may be observed via imaging, and/or may be otherwise sensed by the user of the apparatus. (For example, a sudden "jerk" may indicate that the loop has moved into the appendage.) In response to the distal end of the loop reaching the opening, the opening is identified.

Figure 6B:
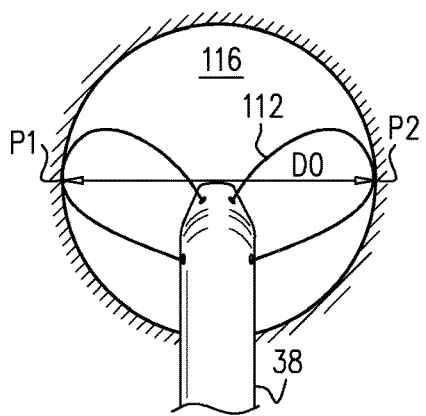

FIGS. 6B-E show the measuring of the opening, following the identification thereof. In FIG. 6B, loops 112 are expanded until they contact at least two points P1 and P2 on a perimeter of the opening. Then, the distance D0 between the points is measured, by using imaging to view the loops while they are in contact with the points. (For example, as described above, the loop(s) may be radiopaque, and fluoroscopic imaging may be used.) In some applications, alternatively or additionally to using imaging, D0 is measured by utilizing markers on proximal portions of the loops (i.e., on proximal portions of longitudinal members 124) that indicate the extent to which the loops have been expanded. In some applications, multiple measurements of D0 are taken for respective multiple contact points, and the diameter of the opening is ascertained from the multiple measurements.

Figure 6C:
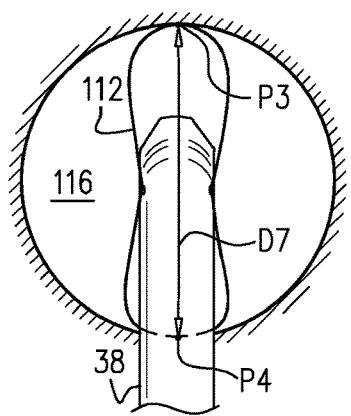

In some applications, as shown in FIG. 6C, a distance D7 that is perpendicular to D0 is measured, alternatively or additionally to measuring D0. An advantage of measuring D7 in addition to D0 is that both the "width" and the "height" of the opening may be measured, such that a more precise assessment of the size of the opening may be made, relative to if only a single distance were measured. In addition, both distances together give some indication as to the shape of the opening; for example, it may be ascertained that the opening is slightly elliptical. In some applications, D7 is measured by deploying loops that expand as shown in FIG. 6C, until the loops contact a second pair of points P3 and P4 on the perimeter of the opening. In other applications, the catheter is rotated about its longitudinal axis by approximately 90 degrees, relative to its orientation in FIG. 6B, and the loops are adjusted until they contact points P3 and P4.

Figure 6D:
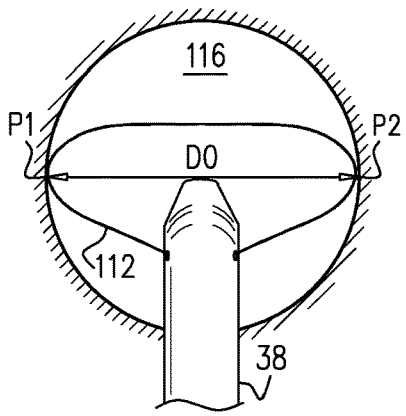
Figure 6E:
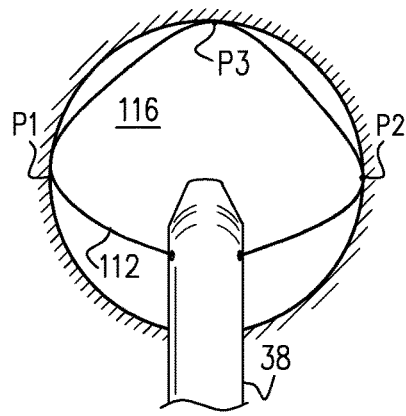

FIGS. 6D-E show applications in which a single loop is deployed. The single loop may be used to measure D0 or D7, as shown in FIG. 6D. Alternatively or additionally, the loop can be used to measure the approximate half-circumference of the opening, as shown in FIG. 6E, by contacting at least three points distributed along the half-circumference of the opening, and summing the distances between successive pairs of points.

In some applications, at least one of loops 112 is also a fossa-ovalis-finding loop, i.e., the at least one of the loops is used both for finding the fossa ovalis and, following the puncture or the fossa ovalis and insertion of the catheter into the left atrium, for finding and/or measuring the LAA. In such applications, longitudinal member 124 may be identical to the longitudinal member described hereinabove with reference to FIGS. 1A-D. In other applications, a first loop is used to find the fossa ovalis, and a second, different loop is used to find and/or measure the LAA.

In some applications, the measurement of the opening is used to select an implant of an appropriate size. The implant is then passed through the catheter, delivered to the opening, and implanted in the opening. For example, some subjects are in need of an LAA-closure implant, i.e., an implant that fills the LAA opening and generally isolates the LAA from the rest of the left atrium. Without prior measurement of the LAA opening, it is possible that an inappropriately-sized implant, which does not properly close the LAA, may be implanted. Hence, the measurement of the opening, as described hereinabove, facilitates the selection of an appropriately-sized implant. Furthermore, the measurement apparatus also functions as a delivery apparatus, such that the measurement, and the delivery may be performed during the same procedure, with only a single insertion of the catheter into the atrium.

Reference is now made to FIG. 7, which is a flowchart for a method for implanting an implant in an LAA of a subject, in accordance with some applications of the present invention. First, at a first insertion step 130, the catheter is inserted into the right atrium. Then, at a first deployment step 132, at least one fossa-ovalis-finding loop is deployed from the wall of the catheter, e.g., as described hereinabove with reference to FIG. 1B. At a first moving step 134, the fossa-ovalis-finding loop is moved along the interatrial septum, until the fossa-ovalis-finding loop contacts the fossa ovalis, as shown in FIG. 1B. Then, at a puncturing step 136, the fossa ovalis is punctured by passing a puncturing element out of the distal end of the catheter, e.g., as described hereinabove with reference to FIG. 10. The catheter is then inserted into the left atrium at a second insertion step 138, and, at a second deployment step 140, at least one appendage-finding loop is deployed. (As described hereinabove, the fossa-ovalis-finding loop may also serve as an appendage-finding loop.) At a second moving step 142, the appendage-finding loop is moved along the arterial wall, as described hereinabove with reference to FIG. 6A. Following the identification of the LAA, the LAA is measured at a measuring step 144, as described hereinabove with reference to FIGS. 6B-D. In response to the measuring, an appropriately-sized implant is selected, at an implant-selection step 146. Finally, the implant is delivered to the LAA at a delivery step 148, and is implanted in the opening of the LAA at an implanting step 150.

Figure 8B:
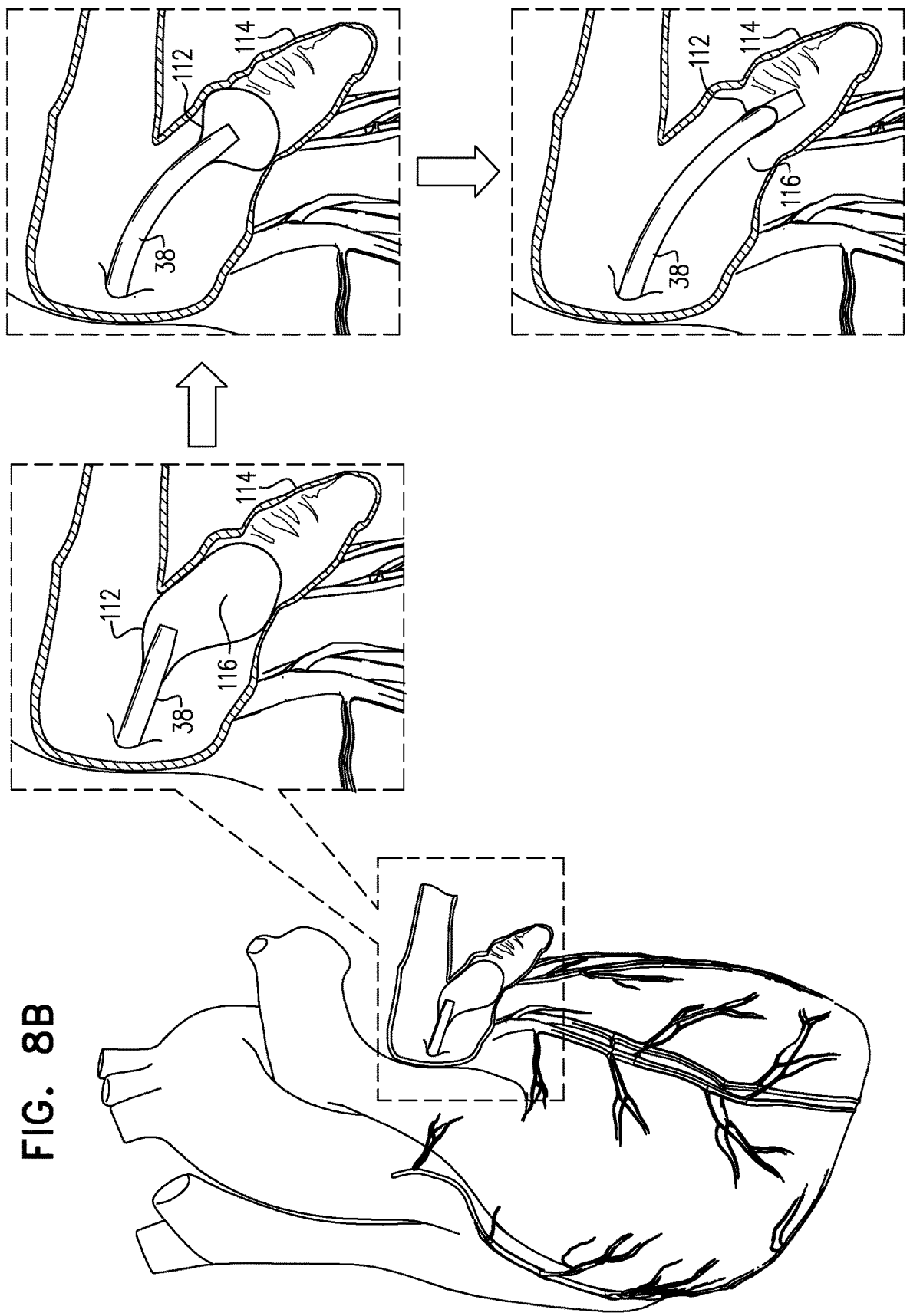
Figure 8C:
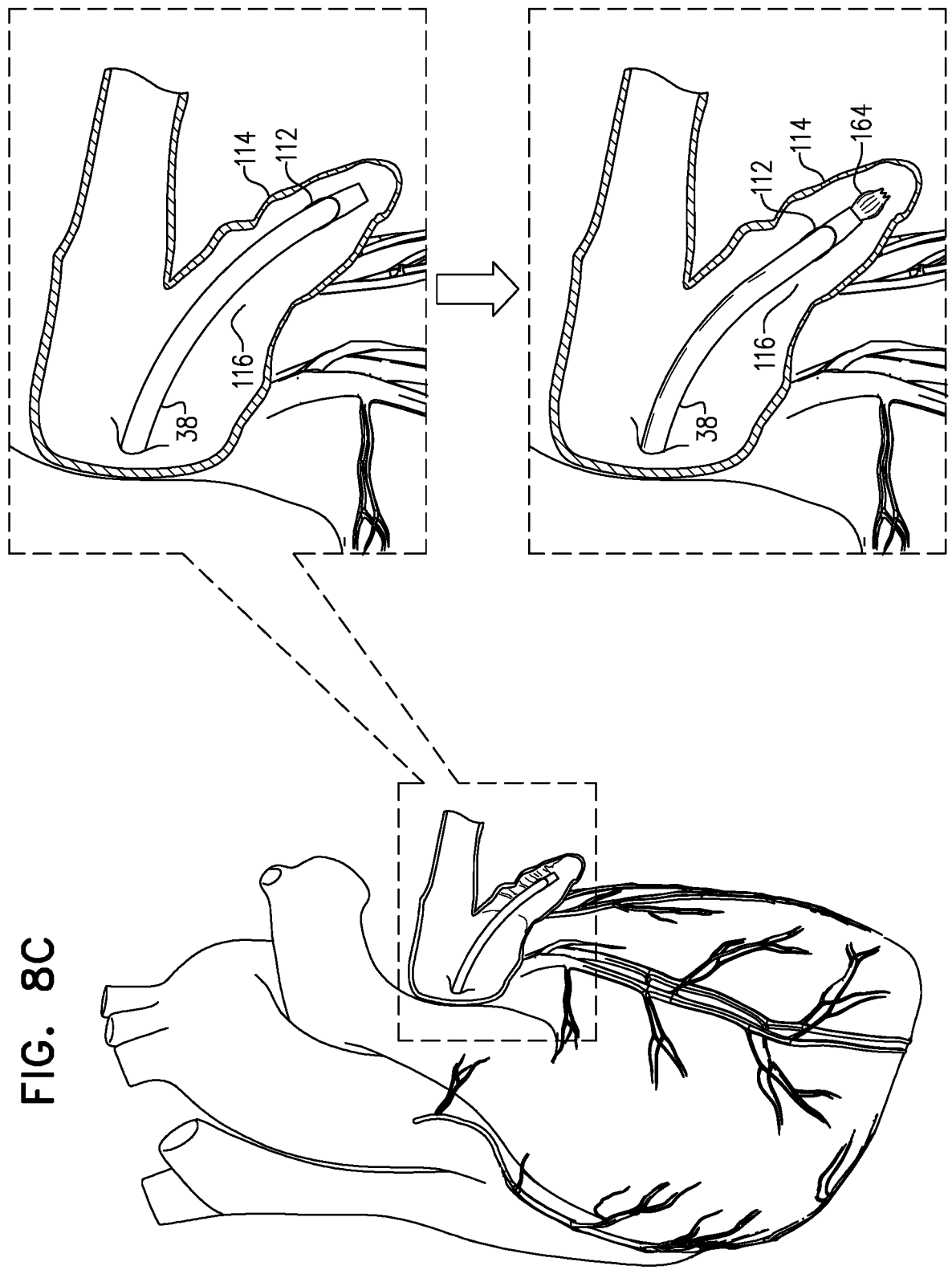
Figure 8D:
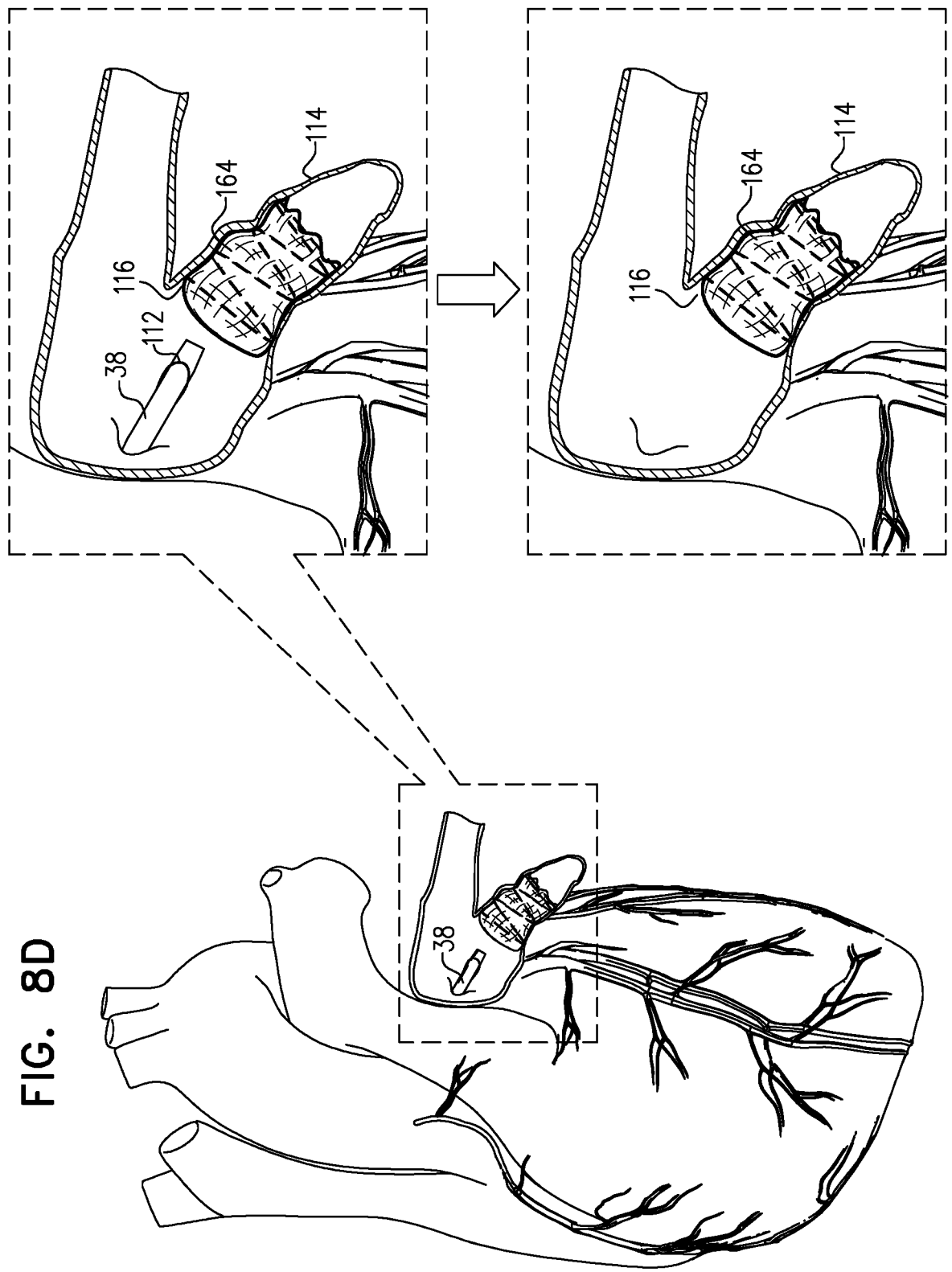
Figure 9:
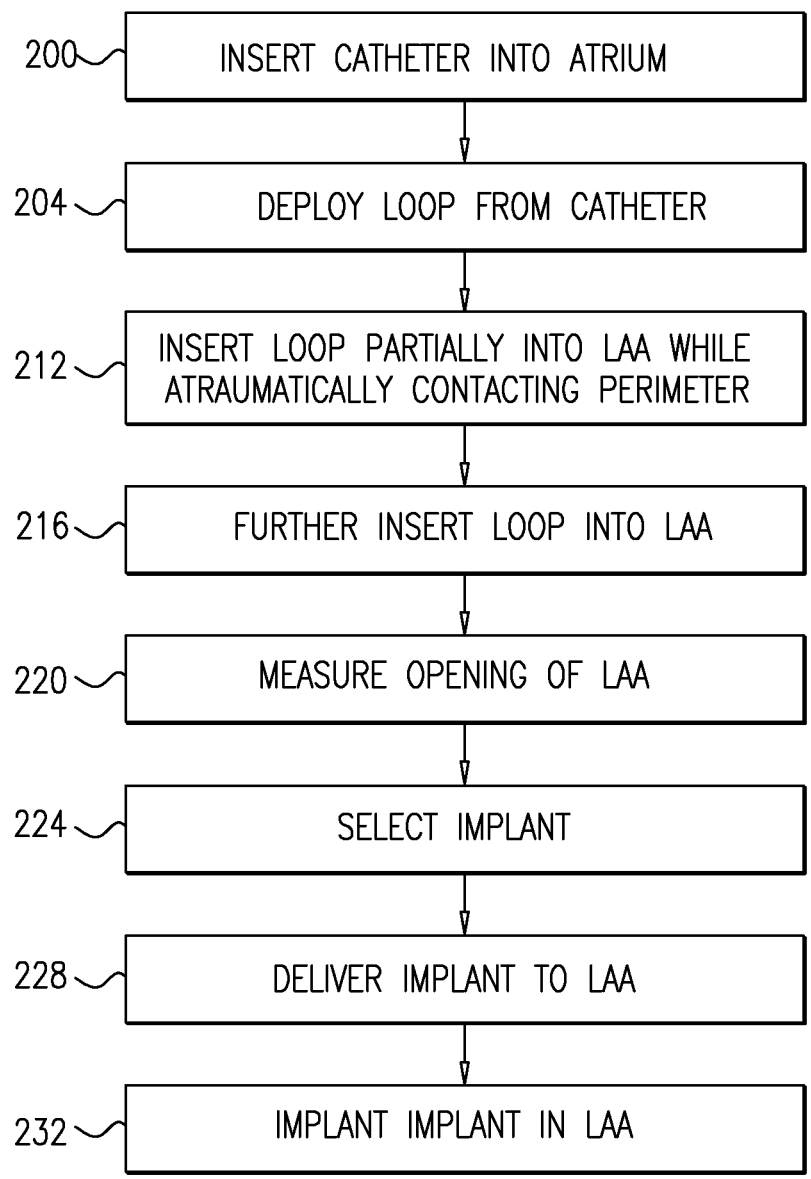
FIG. 9 is a flowchart illustrating a method for implanting an implant in the LAA, in accordance with an application of the present invention.

Reference is now made to FIGS. 8A-D, which are schematic illustrations of a method for finding and/or measuring an opening 116 of appendage (e.g., LAA) 114, in accordance with some applications of the present invention, and to FIG. 9, which is a flowchart illustrating a method for implanting an implant in appendage (e.g., LAA) 114, in accordance with an application of the present invention. As shown in the upper blow-up of FIG. 8A, catheter 38 is inserted into an atrium, such as a left atrium, of a subject, at a catheter insertion step 200 (FIG. 9). As shown in the lower blow-up of FIG. 8A, at least one loop 112 (e.g., exactly one loop 112, as shown, or two or more loops, such as shown in FIG. 6A) is deployed from a wall (typically, a lateral wall 39) of catheter 38, such that a distal end of loop 112 is distal to a distal end of catheter 38, at a loop deployment step 204 (FIG. 9). For some applications, loop 112 is deployed such that a normal to a plane defined by the loop intersects a line that is parallel to a longitudinal axis of the catheter at an angle that is between 10 and 90 degrees, such as described hereinabove with reference to FIGS. 5A-B, mutatis mutandis.

Loop 112 is typically used to find opening 116. Optionally, a location of the opening is identified by imaging the atrium and the appendage. A distal end of loop 112 is moved along the wall of the atrium, typically while being imaged. (For example, the loop may be radiopaque, and fluoroscopic imaging may be used to view the loop.) Loop 112 is partially inserted into appendage 114. While the loop is being inserted, a portion of loop 112 may atraumatically contact a portion of a perimeter 160 of opening 116 of appendage 114, at perimeter-contacting step 212 (FIG. 9). Loop 112 thus functions as a bumper, thereby preventing accidental perforation of appendage 114 which may cause tamponade. For some applications, when the portion of loop 112 atraumatically contacts the portion of perimeter 160 of opening 116, the portion of loop 112 locally bends against the portion of the perimeter of the opening. Thereafter, loop 112 is further inserted into appendage 114, as shown in the upper blow-up of FIG. 8B, at a further insertion step 216 (FIG. 9). Alternatively, during some procedures, the loop may be directly inserted into appendage 114 without first contacting perimeter 160. In any event, opening 116 has been identified, typically using loop 112.

For some applications, a size of opening 116 of appendage 114 is measured using loop 112, such as using the techniques described hereinabove with reference to FIGS. 6B, 6C, 6D, and/or 6E, at an opening measurement step 220 (FIG. 9). For some applications, the measurement of opening 116 is used to select an implant 164 of an appropriate size, at an implant selection step 224 (FIG. 9).

For some applications, the distal end of catheter 38 is advanced into appendage 114, optionally using loop 112 for guidance, such as shown in the middle blow-up of FIG. 8B. Thereafter, loop 112 is retracted against wall 39 of catheter 38, leaving the distal end of catheter 38 in appendage 114, as shown in the lower blow-up of FIG. 8B. Alternatively, loop 112 is retracted before the distal end of catheter 38 is advanced into appendage 114 (not shown). The distal end of catheter 38 may then be further advanced into appendage 114, as shown in the top blow-up of FIG. 8C.

Implant 164 is deployed from catheter 38 to appendage 114, as shown in the lower blow-up of FIG. 8C, at an implant delivery step 228 (FIG. 9). Implant 164 is implanted at least partially in appendage 114, as shown in the upper blow-up of FIG. 8D, at an implant implantation step 232 (FIG. 9). For example, implant 164 may be advanced through catheter 38, either directly within catheter 38, or within a smaller, inner delivery catheter that is advanced through catheter 38 (configuration not shown). For example, some subjects are in need of an LAA-closure implant, i.e., an implant that fills the LAA opening and generally isolates the LAA from the rest of the left atrium. Without prior measurement of the LAA opening, it is possible that an inappropriately-sized implant, which does not properly close the LAA, may be implanted. Hence, the measurement of the opening, as described hereinabove, facilitates the selection of an appropriately-sized implant. Furthermore, the measurement apparatus also functions as a delivery apparatus, such that the measurement and the delivery may be performed during the same procedure, with only a single insertion of the catheter into the atrium.

Typically, the method does not comprise inserting a guidewire into appendage 114, such as for guiding the distal end of the catheter into the appendage. Conventional LAA implantation techniques typically require inserting a guidewire into the appendage in order to guide a catheter into the appendage.

In both the techniques described herein and conventional techniques, a guidewire is typically used to advance a transseptal puncture system across the interatrial septum into the left atrium. Prior to the puncture the guidewire is replaced with a transseptal needle. After the septum has been punctured by the needle (and the needle has been removed), such as described hereinabove with reference to FIG. 1D, this guidewire is reinserted into the transseptal puncture system. The size and shape of this guidewire are constrained by the transseptal puncture inner diameter and maneuverability requirements. The transseptal puncture system is withdrawn from the left atrium while the guidewire is left inside the left atrium. The LAA delivery system is introduced to the left atrium over the guidewire which was left there in conventional LAA implantation techniques, unlike some techniques described herein, after the LAA-implant delivery system has been advanced into the left atrium, the guidewire is withdrawn and replaced with a second guidewire. This second guidewire typically has a larger diameter than the first guidewire, and has a pigtail which can be used effectively to engage the LAA with low risk of perforation. After the LAA has been engaged using the second guidewire, the second guidewire is withdrawn to make space for the implant catheter. This conventional approach thus requires the use of two separate guidewires, which causes the implantation procedure to be longer and more complex.

For some applications, at least one of loops 112 is also a fossa-ovalis-finding loop, i.e., the at least one of the loops is used both for finding the fossa ovalis and, following the puncture of the fossa ovalis and insertion of the catheter into the left atrium, for finding and/or measuring the LAA. In such applications, longitudinal member 124 may be identical to the longitudinal member described hereinabove with reference to FIGS. 1A-D. In other applications, a first loop is used to find the fossa ovalis, and a second, different loop is used to find and/or measure the LAA. For some applications, each of loop (s) 112 includes a longitudinal member that passes through a first opening and a second opening in catheter wall 39, and each of loop(s) 112 is deployed by passing the longitudinal member through at least one of the first and second openings.

In general, apparatus described herein may be used, and techniques described herein may be practiced, in combination with apparatus and techniques described in the following patent application publications, all of which are incorporated herein by reference:

US Patent Application Publication 2014/0309675 to Maisano et al.,

PCT Publication WO 2014/170890 to Maisano et al.,

US Patent Application Publication 2014/0309678 to Maisano et al.,

US Patent Application Publication 2014/0309679 to Maisano et al,

US Patent Application Publication 2016/0100859 to Sapir et al., and

PCT Publication WO 2016/059638 to Sapir et al.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A method for measuring an opening of an appendage of an atrium of a subject, the method comprising:
  inserting a catheter into the atrium of the subject using a transvenous approach;
  thereafter, deploying at least one loop from a wall of the catheter, such that a distal end of the loop is distal to a distal end of the catheter; and
  thereafter, using the loop to measure the opening of the appendage.

2. The method according to claim 1, wherein deploying the loop from the wall of the catheter comprises deploying the loop from a lateral wall of the catheter.

3. The method according to claim 1, wherein the method comprises measuring an opening of an appendage of a left atrium of the subject.

4. The method according to claim 1, wherein deploying the loop comprises deploying the loop such that a normal to a plane defined by the loop intersects a line that is parallel to a longitudinal axis of the catheter at an angle that is between 10 and 90 degrees.

5. The method according to claim 1, wherein the method further comprises, before measuring the opening:
  moving the distal end of the loop along a wall of the atrium; and
  identifying the opening in response to the distal end of the loop reaching the opening.

6. The method according to claim 1, further comprising:
  in response to the measuring, selecting an implant of an appropriate size;
  delivering the implant to the opening, by passing the implant through the catheter; and
  implanting the implant in the opening.

7. The method according to claim 5, wherein identifying the opening in response to the distal end of the loop reaching the opening comprises:
  sensing loss of contact of the loop with the wall of the atrium upon the loop reaching the opening.

8. The method according to claim 5, wherein identifying the opening in response to the distal end of the loop reaching the opening comprises:
  sensing lunging of the loop into the appendage upon the loop reaching the opening.

* * * * *